United States Patent [19]
Pell et al.

[11] Patent Number: 4,945,898
[45] Date of Patent: Aug. 7, 1990

[54] POWER SUPPLY

[75] Inventors: James W. Pell, Los Altos; Richard E. Spielmaker; Arthur W. Zikorus, both of San Jose, all of Calif.

[73] Assignee: Diasonics, Inc., Milpitas, Calif.

[21] Appl. No.: 379,573

[22] Filed: Jul. 12, 1989

[51] Int. Cl.$^5$ .............................................. A61B 17/22
[52] U.S. Cl. ................................ 128/24 A; 606/128; 310/317
[58] Field of Search ........... 128/24 A, 24 EL, 660.03, 128/660.01; 606/127, 128; 310/317; 318/316; 367/137, 142, 155, 157, 903

[56] References Cited

U.S. PATENT DOCUMENTS

| | | | |
|---|---|---|---|
| 2,488,290 | 11/1949 | Hansell | 310/317 |
| 3,129,366 | 4/1964 | Fry | 318/116 |
| 3,942,531 | 3/1976 | Hoff et al. | |
| 3,958,559 | 5/1976 | Glenn et al. | |
| 4,311,147 | 1/1982 | Hauser | |
| 4,315,514 | 2/1982 | Drewes et al. | |
| 4,376,255 | 3/1983 | Kleinschmidt | 310/317 |
| 4,539,989 | 9/1985 | Forssmann et al. | |
| 4,570,634 | 2/1986 | Weiss | |
| 4,586,512 | 5/1986 | Do-huu et al. | 128/660.03 |
| 4,617,931 | 10/1986 | Dory | |
| 4,618,796 | 10/1986 | Riedlinger | |
| 4,622,969 | 11/1986 | Forssmann et al. | |
| 4,655,205 | 4/1987 | Hepp et al. | |
| 4,658,828 | 4/1987 | Dory | |
| 4,664,111 | 5/1987 | Reichenberger | |
| 4,669,483 | 6/1987 | Hepp et al. | |
| 4,674,505 | 6/1987 | Pauli et al. | |
| 4,718,421 | 1/1988 | Rohwedder et al. | |
| 4,749,897 | 6/1988 | Natsume et al. | 310/317 |
| 4,767,959 | 8/1988 | Sakakibara et al. | 310/317 |
| 4,771,787 | 9/1988 | Wurster et al. | 128/660.03 |
| 4,803,995 | 2/1989 | Ishida et al. | 128/660.03 |

FOREIGN PATENT DOCUMENTS 0018614 12/1980 European Pat. Off.

OTHER PUBLICATIONS

Blume, Elain, *Sound, shock waves shatter kidney stones*, Journal of the American Medical Association (JAMA), May 13, 1983, vol. 249, No. 18, pp. 2434-2435.

Mulley, Jr., Albert G., *Shock-Wave Lithotripsy*, The New England Journal of Medicine, Mar. 27, 1986, vol. 314 No. 13, pp. 845-847.

SearVass, MD, Cory, *First German Kidney Stone Crusher Arrives in U.S.*, Saturday Evaning Post, Mar. '84, pp. 50-112.

Goldsmith, Marsha F., *ESWL Now Possible for Patients with Pacemakers*, JAMA, Sep. 11, 1987, vol. 258 No. 10, p. 1284.

Goldsmith, Marsha F., *Stones are Crushed and Many Patients Elated by Results of New ESWL Therapy*, JAMA, Jul. 25, 1986, vol. 256 No. 4, pp. 437-439.

Sauerbruch, Tilman et al., *Fragmentation of Gallstones by Extracorporeal Shock Waves*, New England Journal of Medicine, Mar. 27, 1986, vol. 314, No. 13, pp. 818-822.

Sackmann, MD., Michael, *Shock-Wave Lithotripsy of Gallbladder Stones*, New England Journal of Medicine, Feb. 18, 1988, vol. 318 No. 7, pp. 393-397.

Goldsmith, Marsha F., *Biliary, as Well as Urinary, Calculi Become the Targets of New, Improved Shock Wave Lithotripsy*, JAMA, Sep. 11, 1987, vol. 258, No. 10, pp. 1282-1285.

(List continued on next page.)

Primary Examiner—Francis Jaworski
Assistant Examiner—John D. Zele
Attorney, Agent, or Firm—Blakely, Sokoloff, Taylor & Zafman

[57] ABSTRACT

A pulsed power supply for providing power to a piezoelectric crystal. The power supply provides power to the piezoelectric crystal causing contraction of the crystal. Upon reaching a predetermined degree of contraction, the electrical voltage form the power supply is removed from the piezoelectric crystal by creating a short-circuit between the power supply and the crystal. Removal of electrical voltage from the crystal causes the immediate expansion of the crystal and a resulting energy wave.

1 Claim, 7 Drawing Sheets

OTHER PUBLICATIONS

Piezolith 2300 with dual scanner location system, Richard Wolf, EPL Extracorporeal Piezolectric Lithotripsy, painless Stone Destruction, Advertising Brochure.

Piezoelectric Lithotripsy, The Wave of the Future, EDAP International Corp. Advertising Brochure.

SONOLITH 2000 Extracorporeal Shock Wave Lithotripter, Technomed International Product Brochure.

MPL9000, Dornier Lithotriper, DORNIER MEDIZINTECHNIK, Techical Brochure & System Description.

EDAP LT-01 Extra-Corporeal Lithotripte, EDAP-ESWL, Product Bochure with Technical Specifications.

LITHOSTAR Multifunctinal Renal Examination Unit for Urological Therapy and Diagnosis, Siemens, Product Brochure.

MFL5000, Dornier Medical Systems, Product Brochure and Investigational Device.

MFL5000, Dornier Medical Systems, Technical Description and Investigational Dornier Multifunction Kidney Lithotriper.

Tripter X1, Direx, Advertising Product Brochure.

SD-3 Extracorporeal Shock Wave Lithotripter, Northgate Research, Inc., Advertising brochure of "Investigative Device".

HM4 Kidney Lithotripter, Dornier Medical Systems, Product Data Sheet.

1050 ST System, Medstone International, Inc., Advertising Brochure.

Viktorov, I. A., *Sources of High-Intensity Ultrasound Volume 1,* Plenum Press-New York, 1969, pp. 288-305.

Coleman, D. Jackson MD et al., *Therapeutic Ultrasound in the Production of Ocular Lesions,* American Journal of Ophthalmology, Aug. 1978, vol. 86-No. 2, pp. 185-192.

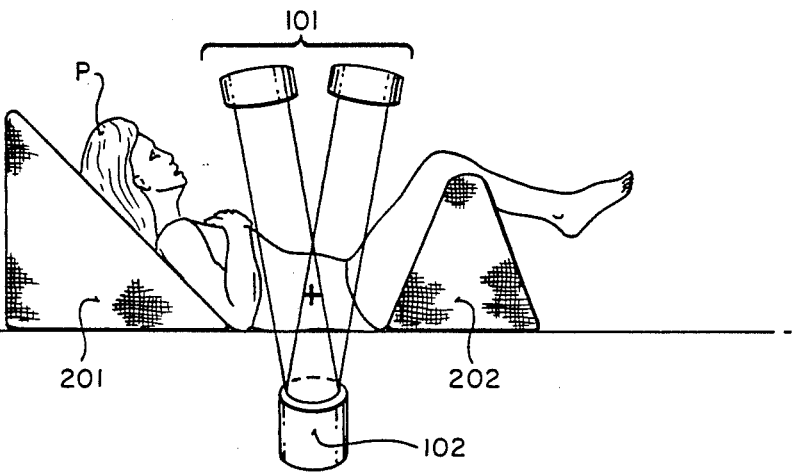
FIG_2A
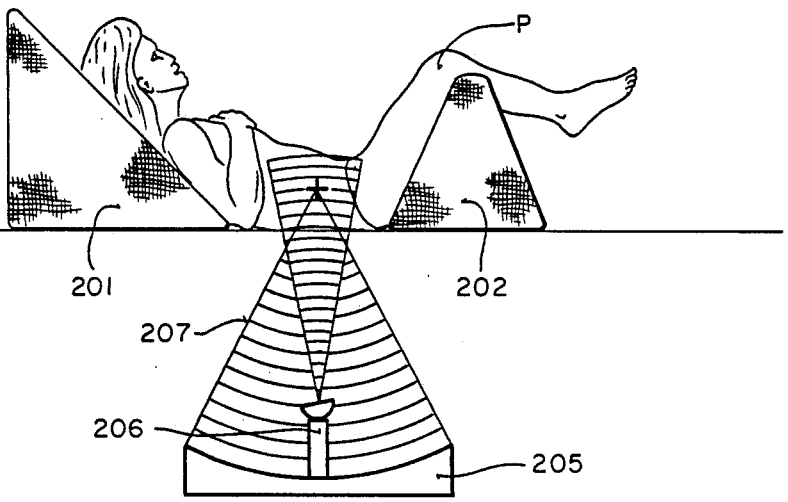
FIG_2B
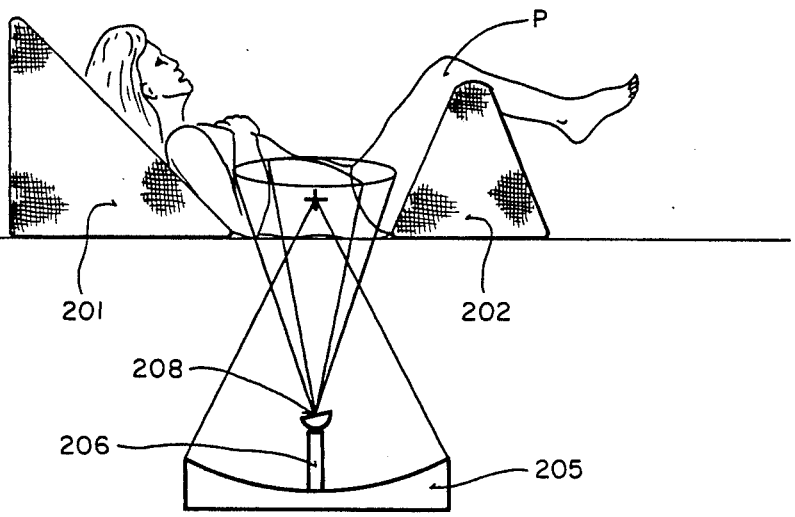
FIG_2C

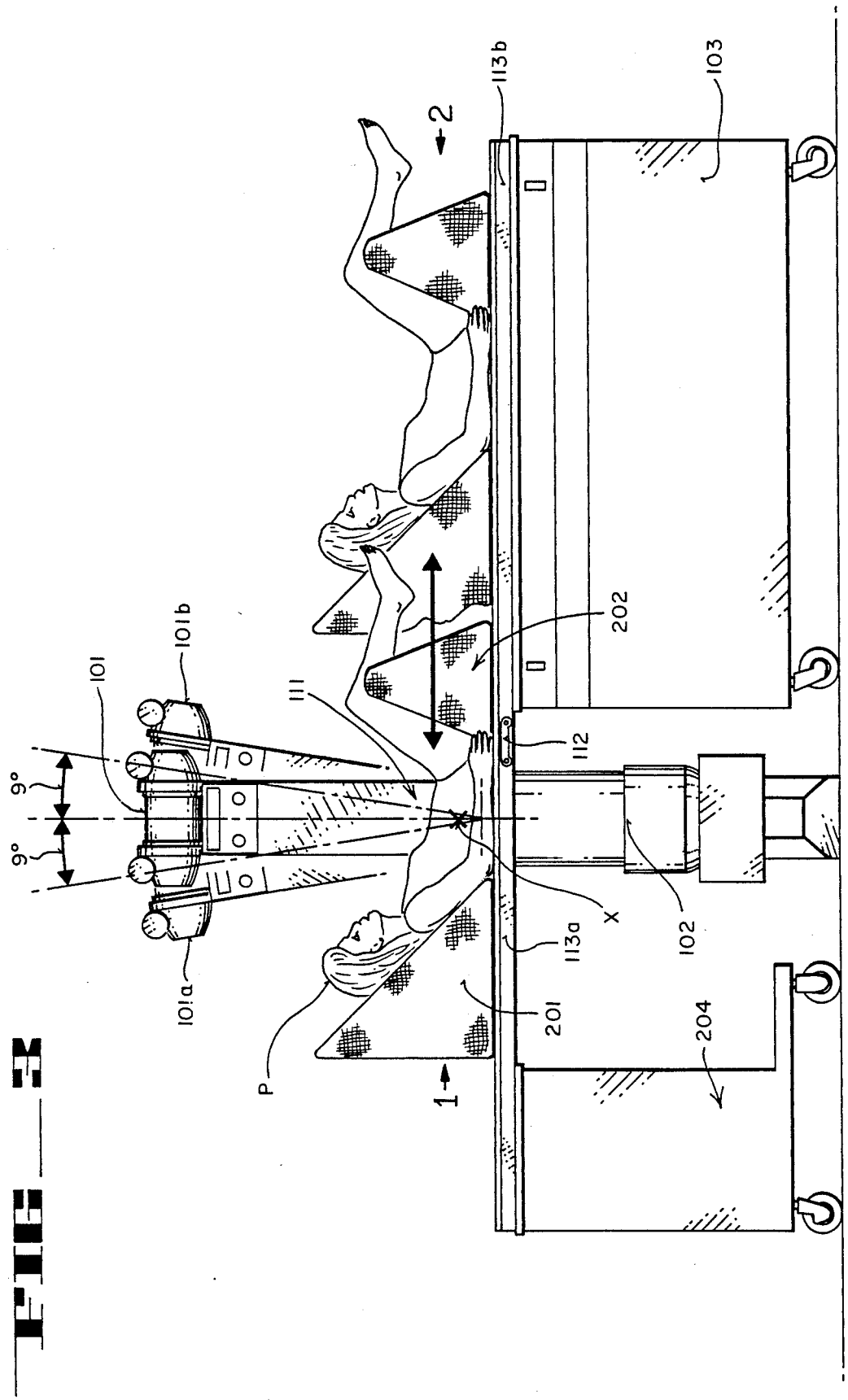

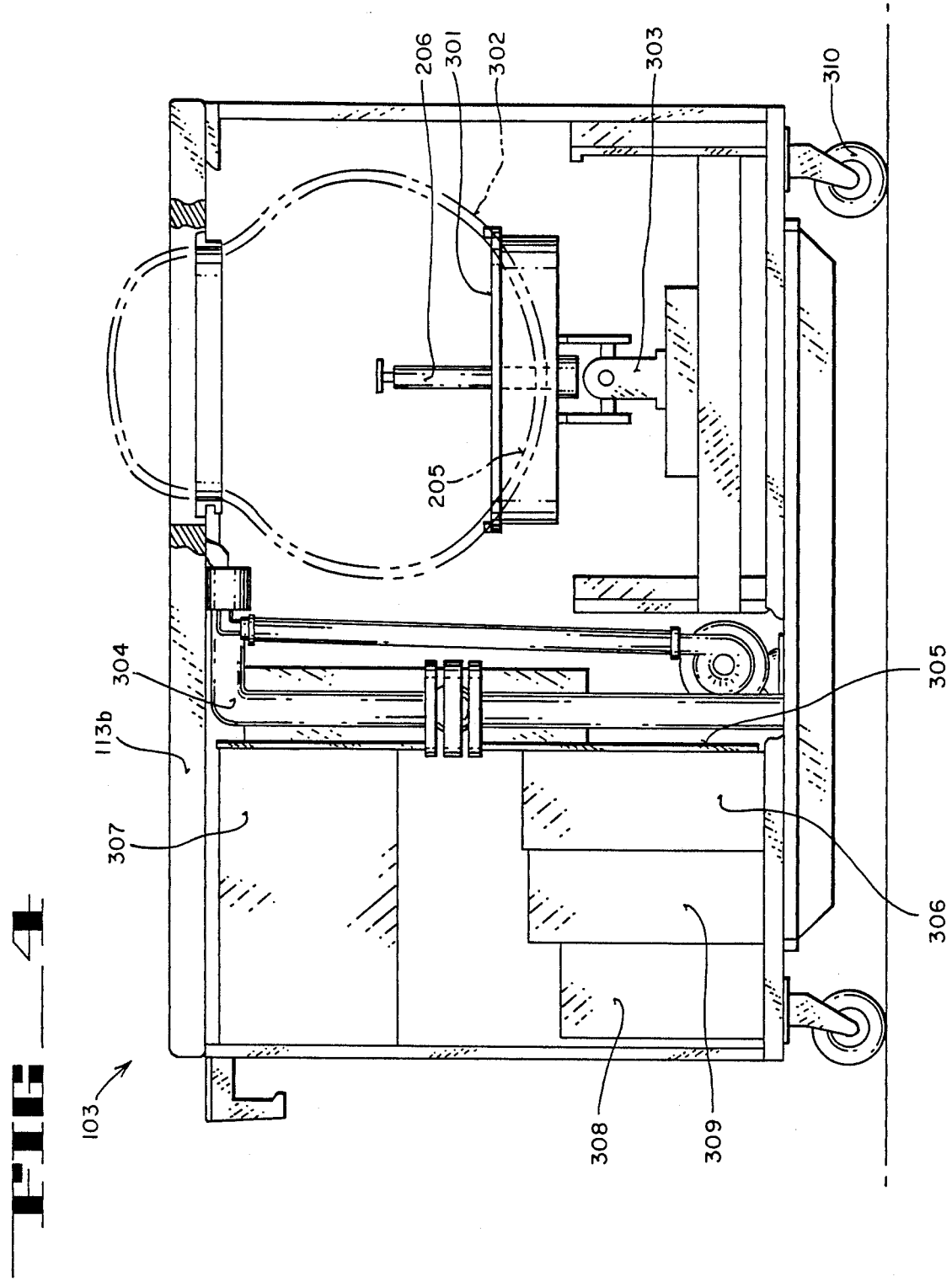
FIG_4

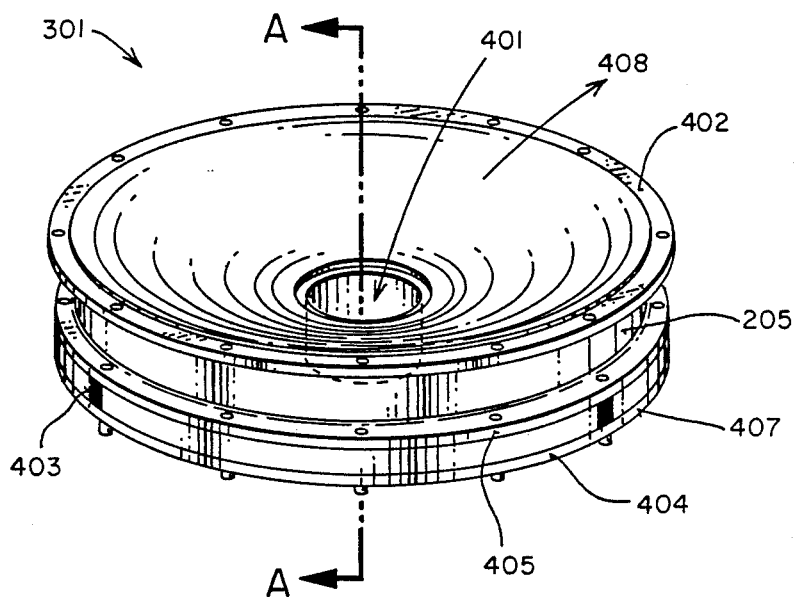
FIG_5
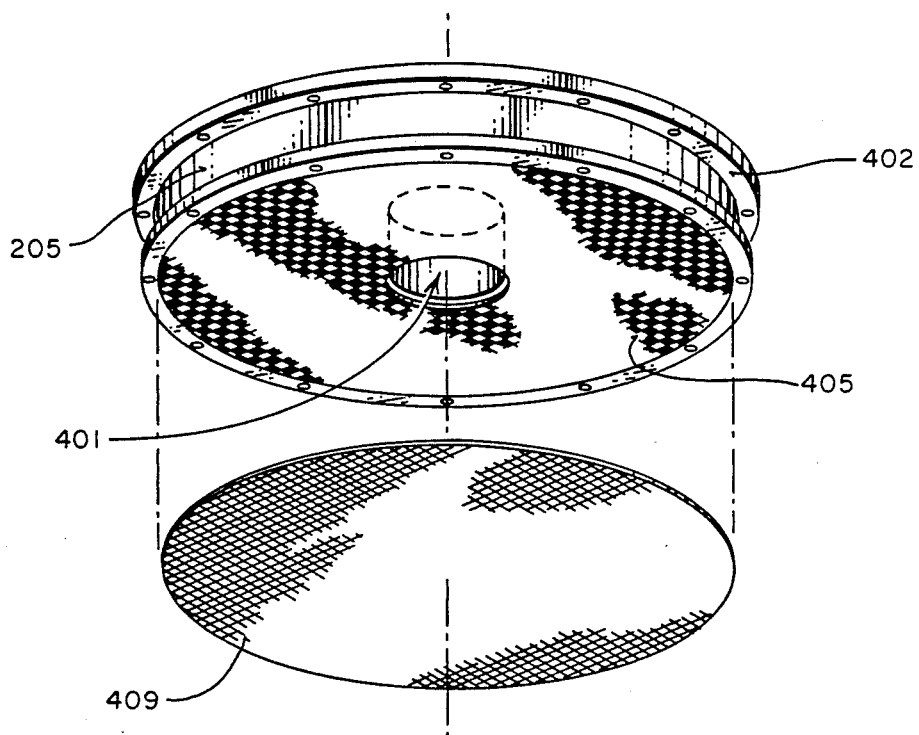
FIG_7

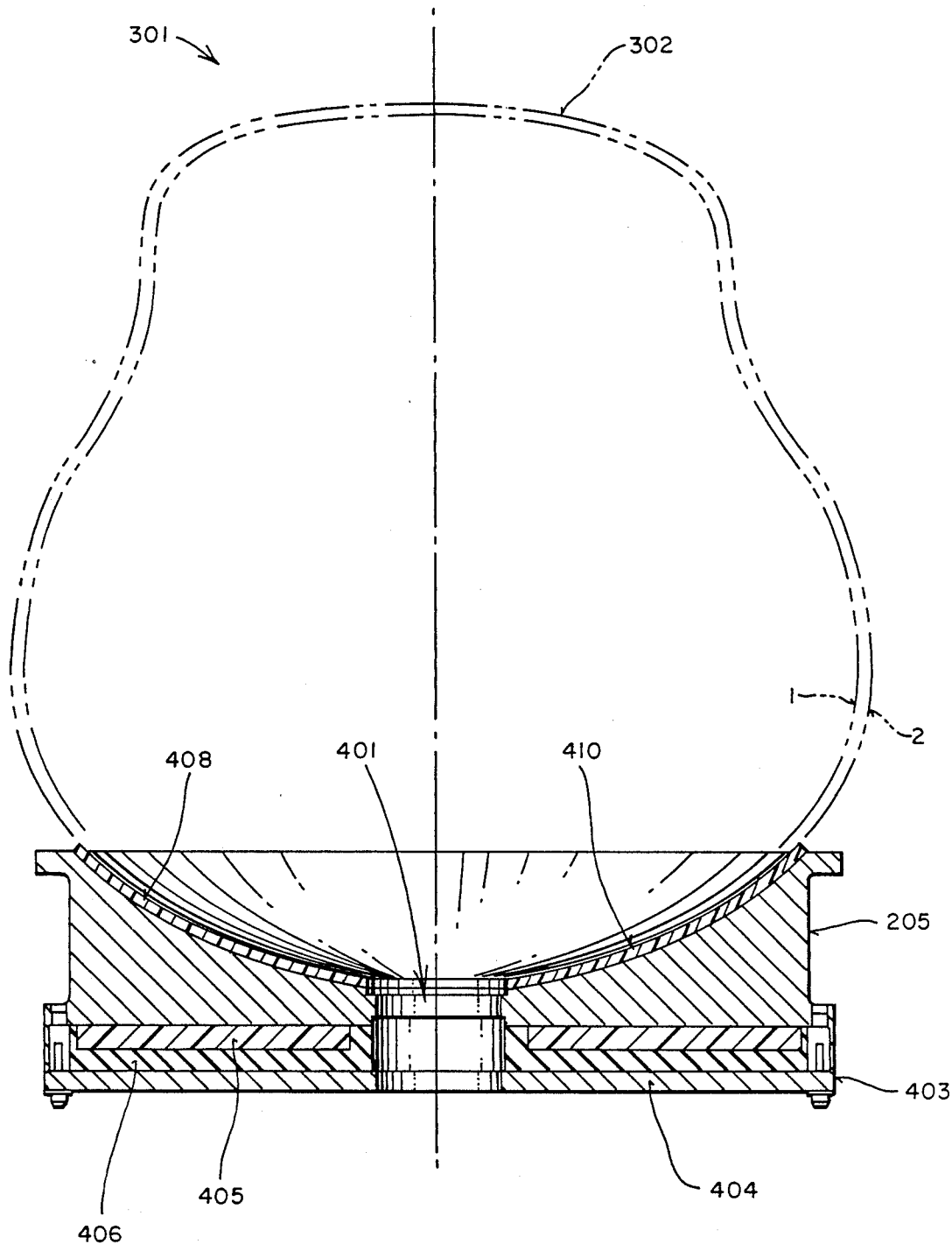
FIG_6
SECTION A-A

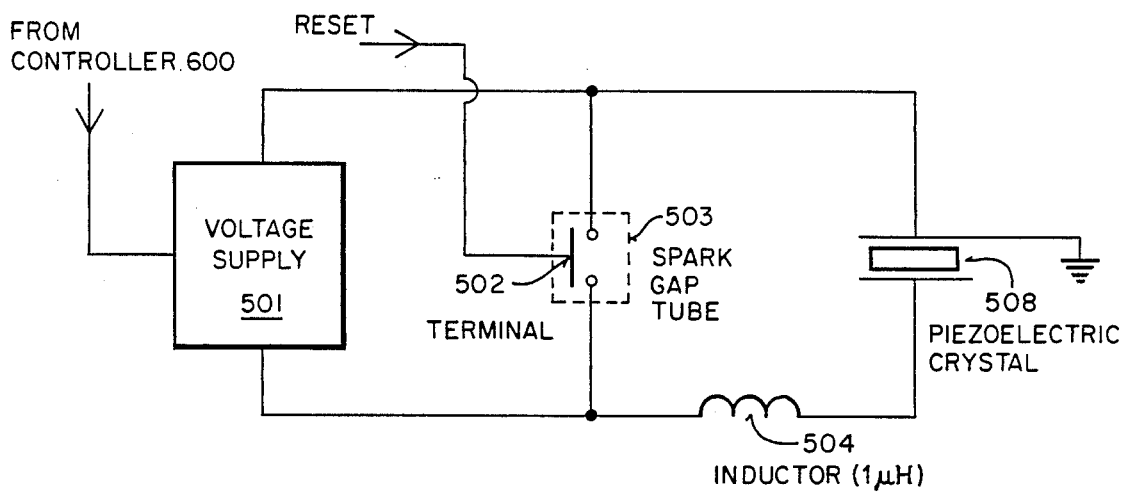
FIG_8
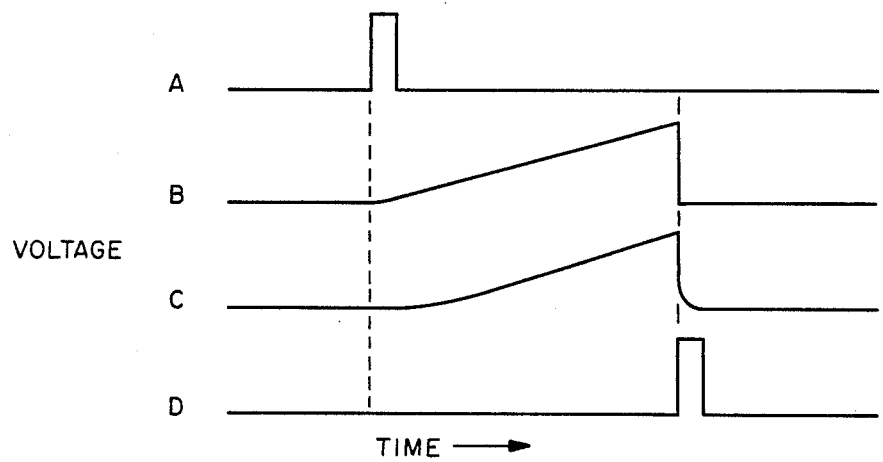
FIG_9
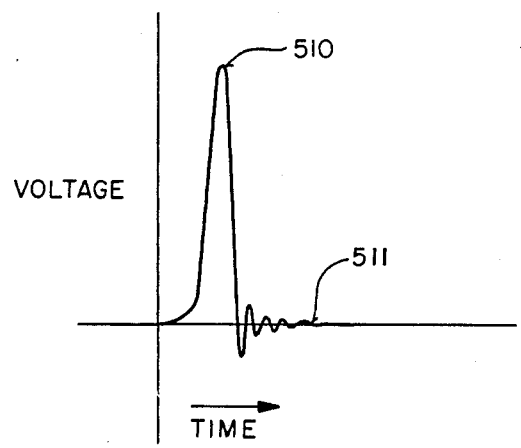
FIG_10

POWER SUPPLY

BACKGROUND OF THE PRESENT INVENTION

1. Field of Invention

The invention relates to an improved apparatus for the contact free disintegration of a calculus located in the body of a human being. In particular, the invention provides improved localization of the calculus and enhances the ability to direct a focussed sonic wave to a target region in the body.

2. Prior Art

Extracorporeal shock-wave lithotripsy in a medical procedure that disintegrates renal (kidney) stones. The term, lithotripsy is derived from the Greek and literally means "stone crushing." This medical "stone crushing" technique has been demonstrated to be effective on renal (kidney), upper ureteral and biliary stones (gallstones) in human patients. The technique is noninvasive and eliminates the need for the more conventional stone removal procedures, such as open surgery.

Stone crushing is achieved by the geometric focussing of energy, such that the area of focus coincides with the stone that is to be shattered. The focussing of energy is a principle that is frequently used to obtain a strong effect within a confined area. The application of focussed energy is effective on the stone, since it is relatively brittle. The application of stress leads to the rapid information of cracks and eventually to the disintegration of the stone.

Although a single intense pulse will generally shatter the stone, a pulse train of lower intensity and short duration pulses will generally produce smaller and more uniform particles. One drawback to a series of pulses is that during treatment the small particles produced during the fragmentation shock waves may obscure the larger remaining fragments. This may result in the shielding of the larger, remaining fragment from the shock wave, which results in an increase of treatment duration.

On the other hand, the accumulated small particles may lead the care provider into prematurely terminating treatment before completion, due to the inability to accurately view the remaining larger fragments.

Another problem associated with the production of small particles, is that gravitational forces may cause the small particles of settle into the lower calyces, thereafter requiring an excessive amount of time to effectuate clearing these lower calyces.

Despite the problems associated with the smaller particles, for the kidney stone patient, there are number of direct benefits from the lithotripsy technique that outweigh these minor disadvantages. The technique is capable of reducing the length of hospital stay from 7 to 14 days for conventional stone removal surgery to 4 days or fewer. It also eliminates the 4 to 6 weeks post-hospitalization convalescence commonly required after major surgery. Typically, the kidney stone patient will naturally and spontaneously pass the stones in the urine, much as if the stones were naturally grain-sized. However, after fragmentation, there will be many more grain-sized stones than occur naturally.

There are several other techniques presently used to treat kidney stones, as an alternative to major surgery. For example, if the stone remains grain-sized, it usually passes spontaneously in the urine and the patient can be treated with drugs to reduce the pain and to prevent future stone occurrence. However, this technique is usually only effective for very small stones.

Depending on the size and the location of the stone, several other clinical and surgical methods are available. If the stone has formed or lodged itself in the lower urinary tract and bladder, a standard cystoscope combined with a stone basket or a special stone removal forceps may be used to extract the stone. During the procedure, a local anesthetic must be administered to minimize the pain. Additional drawbacks are the possibilities that the ureter will be damaged and the formation of additional stones that would prohibit the repetition of the procedure.

Ultimately, if the stone cannot be removed by any of the conventional methods, the patient must resort to open surgery. The traditional surgical procedure is a major operation that requires an incision into the kidney or ureter to remove the stone. In addition to the normal morbidity and risks associated with major surgery, another stone could form, necessitating further surgery. Furthermore, there is a chance that the patient will finally lose the kidney altogether.

As an alternative to open surgery, lithotripsy was explored. However, early lithotriptic treatment employs invasive ultrasonic lithotripsy. The lithotriptic means employed involved an insertion of an ultrasonic probe into a small incision in the patient's side. While this required less recovery time than traditional surgery, it was still surgery, however small the incision and furthermore carried all the inherent risks associated with surgery.

Noninvasive extra corporeal shockwave lithotripsy was developed and overcame the negative risks of surgery. A shock wave is generated and ultimately focussed at the stone. The focussed wave strikes the stone, it disintegrates the stone and the stone fragments are ultimately passed through the ureter.

Early versions of extra corporeal (EC) shock wave lithotripsy required the patient to be immersed in a large tank of water. Originally, a spark gap electrode was fixed at one end of a large stainless steel tub and generated a shock wave as the electrode was discharged underwater. Since the impedance properties of water and soft tissue are similar, the shockwave entered the body without damaging the soft tissue. If care is taken to direct the shockwaves at the calculi, other parts of the body are generally not affected. Typically, bones are not affected by this procedure due to their high tensile strength and the brevity of the pulses. However, the large difference in acoustical impedance between the water and the stone results in enough pressure to shatter the stone. The process was painful and the patient generally required an epidural or general anesthesia.

Before treatment could commence, it was necessary to locate and identify the stone. Prior to immersing the patient into the large stainless steel tank of water, the patient was x-rayed thus prelocalizing the stone. After every 100 pulses or so, the patient was lifted out of the tank and x-rayed again. This was to ascertain the status of the stone and to verify the effectiveness of the treatment. With an average of 1600 pulses, the patient could be x-rayed as many as 17 times to verify that the stone was fragmented and to confirm the completeness of the treatment. Although an x-ray produces a sharper and clearer progess report, the patient was required to undergo a number of detrimental radiation exposures.

Another problem associated with immersing the patient is the inability to accurately reposition the patient once the patient had been moved. Since the electrode is fixed, the patient must be positioned and repositioned. This led to inaccuracies and sometimes painful results.

An alternative localization technique requires the use of two x-ray images, with the focal point at the central point of the two screens. Typically, the two x-ray devices for locating the stone are disposed next to the shockwave generator and reflector and are on an opposite side or axis of the generator. The two central beams of the two x-ray heads intersect the axis of the reflector running through the two focal points. The intersection should be near or at the location of the stone. Establishment of a relationship between a spatially fixed mark and the patient is required. The equipment generally is repositioned vis-a-vis the patient.

From a point of view of expense, the utilization of two x-ray head and devices is relatively expensive to operate and to maintain. There is also the question of the radiation dosage that the patient receives.

When using an x-ray procedure, the patient must be positioned or repositioned such that the stone is located at the focal point of the shock wave. For example, when using a stainless steel water tank, the patient is then positioned with a hydraulic system so that the calculus is at a predetermined focal point. While this allows access to a more accurate target region, it is necessary to physically reposition the patient for each image. Disadvantageously, the patient is required to remain immobilized during the location procedure.

Ultrasound imaging is another suggested alternative means of locating and monitoring the stone. Generally for well-defined stones, ultrasound is sufficient to monitor the progress of treatment. Furthermore, the use of ultrasound eliminates the problems of radiation dosage that arise with the use of x-ray localization techniques.

Another advantage of ultrasound imaging is the ability to monitor real time progression of the treatment. Additional ultrasound monitors can be positioned within the treatment system in such a way as to virtually eliminate repositioning of the patient.

However, ultrasound imaging does not provide the same same high contrast results or "pictures" that an x-ray unit can provide. Since the resulting images are not as sharp and have as high a contrast, which can be due to the limitations to the technique itself, the size and quantity of the stones, or the size of the patient, can make progressive monitoring of patient and the subsequent treatment somewhat risky and haphazardous.

Furthermore, prior to the elimination to the large steel water tank, the use of ultrasonic monitoring equipment was severely limited, as the equipment had to be located within the vicinity of the patient itself.

A combination of the two monitoring techniques, that is x-ray and ultrasound, would be suited except for the problem of patient repositioning. Immobility of the patient is essential and are identical to the problems discussed previously in connection with the x-ray techniques.

The eventual elimination of the large stainless steel water tank resulted in a more compact and effective system. Furthermore, elimination of the water tank also gave rise to the possibility of using ultrasound imaging. Patient immersion became unnecessary as the acoustic waves were still propagated through a water containment bag rather than through an open body of water. The patient is positioned over a cushion or a bag filled with water. The cushion is coupled to a stretcher and to the patient by a layer of ultrasound gel.

Once the patient positioning had been improved, the means for producing the shock wave needed to be improved. For example, the prior method of producing focussed acoustic waves required an electric discharge generated across an underwater spark gap, positioned in the focus line of an elliptical reflector. The early spark gap systems generated a shockwave in a large tank of water, in which the patient had previously been positioned. The process shattered renal stones by a brute force method. The treatment required the patient to have an epidural, spinal or general anesthesia in order "to keep the patient under control, to avoid hurting the patient and to aim better at the stone."

Improvements made it possible to remove the patient from the water tank and to virtually eliminate the need for an epidural or general anesthesia. Generally, a larger ellipsoid for focal precision and a decrease in the power output are credited for the improvements. Accuracy improved as the focussing process was computer controlled, rather than visual sighting by the operator. The computer automatically positions the patient in the shockwave focus by controlling the patient's table.

The spark gap systems create a diverging pulse or explosion. The energy produced is distributed over a relatively large area, for example 15–20 mm square and requires that the energy be focussed within a parabolic reflector. This diverging pulse induces arhythmia, pulverizes tissue and causes bruising. To avoid the inducement of extrasystoles, the shockwave must be released as a function of ECG or respiratory triggering. Furthermore, the spark gap electrodes tend to be somewhat costly.

On the other hand, an alternative means using a piezoelectric transducer generates a converging pulse and eliminates the need for cardiac or respiratory triggering. With a converging pulse system, an area of impact of approximately 2–3 mm square is observed. This results in less tissue damage with approximately the same amount of pressure. Generally, the patient only requires a local or a topical anaesthetic, if any at all.

The piezoelectric crystal is the basis for the piezoelectric transducer. A piezoelectric crystal is a piece of natural quartz or other asymmetric crystalline material capable of demonstrating the piezoelectric effect. Piezoelectricity is a phenomenon first noticed in 1880 whereby certain crystalline substances generate electrical charges when subjected to mechanical deformation. The reverse effect also occurs, that is, a voltage applied across the crystal causes mechanical deformation or flexing.

To produce the shock wave, a piezoelectric crystal is deformed by applying a high frequency, high voltage pulse of the proper polarity, thus causing the crystal to compress. The voltage is then withdrawn from the crystal, such as shorting the crystal to ground and the crystal expands to it's "normal" state. This results in a pressure wave front that propagates through a medium such as water.

Typically, the shock wave is focussed by arranging piezoelectric crystal elements in a mosaic pattern on the surface of a dish generally shaped as a concave lens. The pattern and lens may be designed such that each individual element is excited by a pulse generator simultaneously. Thus, the waves produced by the crystals arrive at the target area focussed and in phase, with a very narrow near ideal shape and with high energy at the focal point. Advantageously, the dish is shaped to produce very small focal areas in which the energy is sufficient to destroy the store but virtually painless.

A major disadvantage of the multi-element piezoelectric system is the necessity of simultaneously triggering 300 to 3000 elements on the concave surface of the focussing lens. Disadvantageously, it is necessary to connect all the piezoelectric crystals to act as one to work in conjunction with a single power supply. An alternative method is to connect each individual element to individual power supplies, for example, having 300 elements and therefore 300 very small, individual power supplies triggering simultaneously. In addition to the problems arising from coordinating all the elements, there is the problem of cost effectiveness.

Another costly disadvantage is the requirement that the numerous elements be specially made. The individual elements must be contoured to fit within the concave configuration of the focussing lens. This decreases the cost effectiveness of the piezoelectric system.

With the use of a piezoelectric transducer, it is necessary to generate a sufficiently high voltage to deform the piezoelectric crystal. Typically, a high voltage generator is required.

In order to ensure that the shockwave generated from the piezoelectric crystal deformation is sufficient to crush the kidney stone, the wave must be focussed. One alternative means of focussing the wave is to create a semi-circular dish wherein the piezoelectric crystals are arranged on the upper surface of the dish in a spherical mosaic-like arrangement.

Generally this type of arrangement requires careful manufacturing of the crystals such that the bottom is rounded as well as the top to maintain a semi-spherical or semi-ellipsoid surface area. Either the crystals can be manufactured so that they fit like a mosaic within the face of the lens or dish or they may be sufficiently small pieces that, because of their size, they merely fit within the shape of the dish itself.

A focussing lens with the crystals configured within the concave surface of the lens produces a very narrow, more ideal shape with a high energy wave at the focal point. This narrowed focussed shockwave requires a shorter duration for the shattering pulse.

The use of a focussing lens with the piezoelectric crystals has several other advantages over that of the spark gap technology. Since the lens creates a converging focussed pulse, the problem of cardiac gating or arhythmia may be eliminated. In contrast, the spark gap generators create a diverging pulse and induce arhythmia. Additionally, there can be much more damage to surrounding tissue as well as substantial bruising and the possibility of passing of blood through urine when using ellipsoid reflectors.

Thus, what is needed is a lithotripsy system for production of a focussed energy wave including a improved power supply for providing voltage to piezoelectric crystals.

SUMMARY OF THE INVENTION

The present invention discloses an lithotripsy system having an improved power supply for supplying pulsed power to a piezoelectric crystal. The crystal responds to application of voltage from the voltage source by contracting. Upon removal of the voltage from the voltage supply, the crystal expands creating a energy wave in front of the crystal. In the preferred embodiment, the energy wave is focussed with a focussing dish and directed for application to a calculus in a living body. This results in the destruction of the calculus.

The power supply apparatus of the present invention comprises a trigger pulse generation for generating trigger pulses. Generation of each trigger pulse results in the eventual production of a focussed energy wave.

The trigger pulse generator is coupled with a voltage supply for supplying voltage to the piezoelectrical crystal. Responsive to each trigger pulse, the voltage supply produces a ramped voltage which is applied to the crystal.

In addition, the ramped voltage is applied to a spark gap tube which, upon application of a predetermined voltage level, causes the voltage supply to short-circuit removing power from the crystal; this removal of power results in the immediate expansion of the crystal and subsequent production of an energy wave.

BRIEF DESCRIPTION OF THE DRAWINGS

FIGS. 2(a)–(c) are schematic representations of the relationship between several components of the lithotripsy system and:
  (a) a representation of a body of a patient to an x-ray component of the lithotripsy system; and
  (b) a representation of the body of the patient to an ultrasonic-real time scan component of the lithotripsy system; and
  (c) a representation of the body of the patient to a ultrasonic shockwave generation component of the lithotripsy system.

FIG. 3 is a perspective view of a patient table and dual tomo-heads of the x-ray component of the lithotripsy system of the preferred embodiment.

FIG. 4 is a cross-sectional representation of a control unit and a stone breaking unit of the lithotripsy system of the preferred embodiment.

FIG. 5 is a detailed top plan perspective view of an acoustical lens assembly of the lithotripsy system of the preferred embodiment.

FIG. 6 is a cross-sectional view of the acoustical lens assembly taken as section A—A of FIG. 5.

FIG. 7 is a bottom plan, exploded, perspective view of piezoelectrical crystals bonded to the acoustical lens and of coupling copper mesh.

FIG. 8 is a circuit diagram of a piezoelectric crystal triggering circuit as may be utilized by the lithotripsy system of the preferred embodiment.

FIG. 9 is a graphic representation of the timing sequence of the triggering circuit of FIG. 8.

FIG. 10 is a graphic representation of the voltage profile from a crystal of FIG. 8.

DETAILED DESCRIPTION OF THE PRESENT INVENTION

Figure 1:
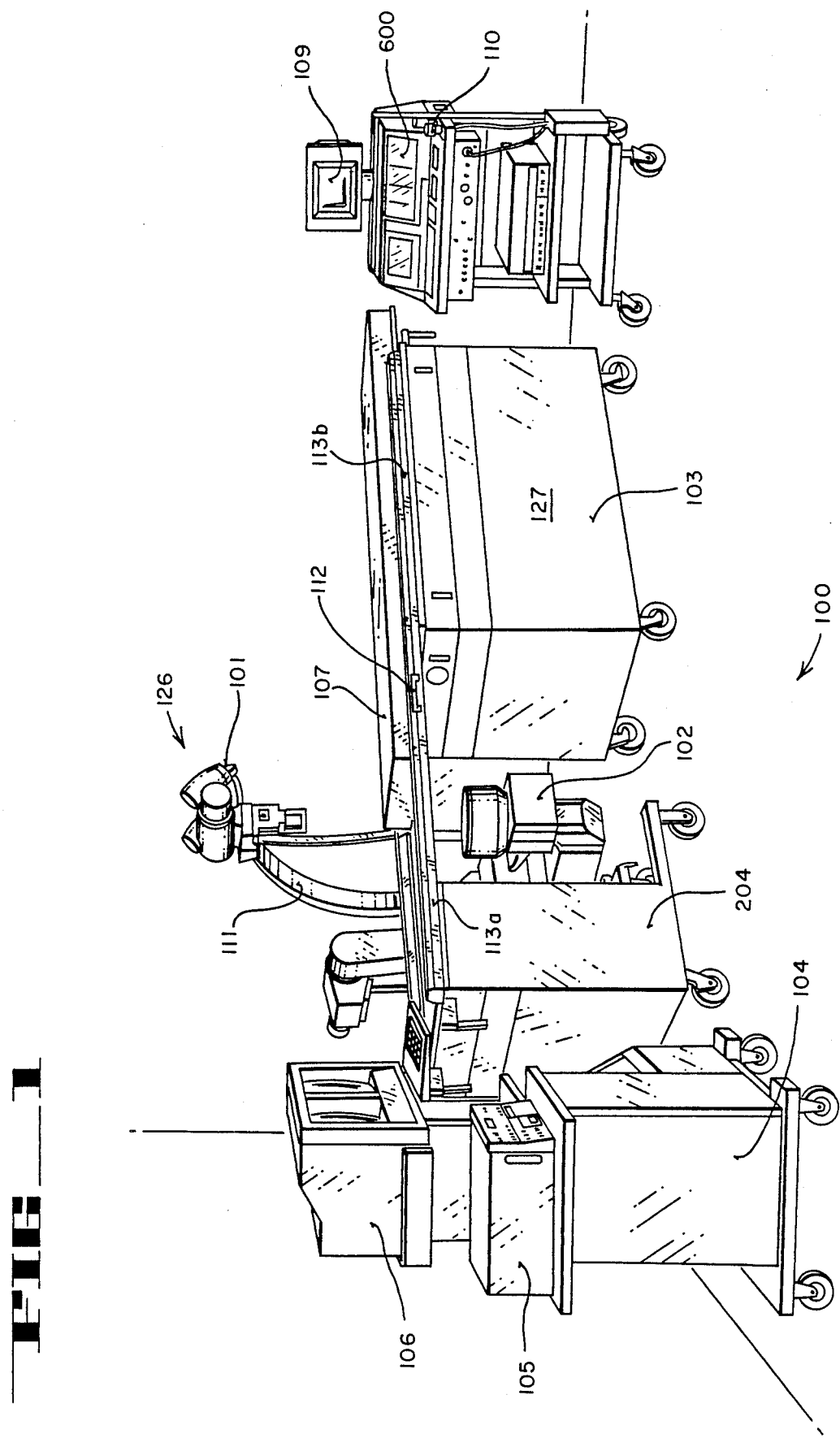
FIG. 1 is a block diagram of a lithotripsy system of the preferred embodiment of the present invention.

An invention is described that provides a means for locating, positioning and for breaking up, without contact, calculi present in the body of a human being. As a result of the capabilities of the present invention, the accuracy and completeness of lithotriptic treatment are effectively enhanced. In the following description, numerous specific details are set forth such as specific dimensions, materials, etc., in order to provide a thorough understanding of the present invention. It will be obvious, however, to one skilled in the art that the present invention may be practiced without these specific details. In other instances, well-known procedures and materials have not been described in detail in order not to unnecessarily obscure the present invention.

Proceeding now to the detailed description of the drawings, FIG. 1 illustrates a perspective overview of the lithotripsy system 100 of the present invention. The lithotripsy system 100 is comprised of an ultrasound imaging unit 125, a mobile x-ray unit 126 and a lithotripter unit 127.

The ultrasound imaging unit 125 is a self-contained system that can be utilized as a stand alone ultrasound unit, in addition to functioning as a real-time ultrasonic imaging system for the lithotripter 100. The ultrasound imaging unit 125 is comprised of a control panel 600, a hand-held imaging probe 110, and a monitoring unit 109.

The x-ray unit 126 provides for fluoroscopic image processing and spot film capabilities. A urological table 113a is docked to a lithotripter table 113b and locked into place by the docking latch 112. Although the preferred embodiment illustrates the use of docking latch 112, any means of stably connecting the two tables together is within the spirit and scope of the present invention. Alternatively, the use of only a single table is also within the scope of the present invention. The urological table 113a can be used as a stand alone examination table for routine urological procedures with or without the use of the x-ray unit 126.

The x-ray unit 126 is comprised of mobile C-arm 111, a pair of fluoro exposure monitors 106, a control unit 105, and a monitor cart 104. Although FIG. 1 preferably illustrates a mobile C-arm 111 as a means for providing fluoroscopic images, a standard x-ray unit is also an acceptable means of providing the necessary fluoroscopic images. The mobile C-arm 111, as well as a standard x-ray unit is typically comprised of a tomo head 101 and a means for receiving fluoroscopic images 102.

Referring to FIGS. 2(a)–(c), the treatment procedure of the lithotripter system 100 of FIG. 1 is schematically shown. FIG. 2a describes the patient P in relationship to the tomo head 101 and means for receiving flouroscopic images 102. The patient P is positioned on a planar surface, with the upper portion of the body inclined upward on a headrest 201. The lower portion of the body is immobilized by placing the patient's knees over a leg rest 202. A dual fluoroscopic image is then obtained by acquiring two oblique images. The oblique images are obtained by moving the tomo-head 101 off axis by +9 degrees and −9 degrees.

FIG. 2(b) describes the patient P in relationship to an acoustical lens 205 of the lithotripter unit 127. (The acoustical lens 205 will be described in more detail with reference to FIGS. 5-7.) The patient P, still positioned on the planar surface and the headrest 201 and leg rest 202 are moved from one end of a treatment table to the other end of the table. An ultrasound probe 206 is positioned centrally within the lens 205. A focussed shockwave 207 is directed at the kidney stone previously located by the dual fluoroscopic images as described in FIG. 2(a). FIG. 8 describes the pre-location procedure in more detail.

FIG. 2(c) describes the patient P in relationship to an ultrasound imaging probe 206 of the lithotripter unit 127. The imaging probe 206 is, preferably, centrally located in the acoustical lens 205, allowing for ultrasound localization and real-time monitoring. The central location of the imaging probe 206 provides a multizone focussing array 208 allowing for an extended field-of-view.

Referring to FIGS. 1 and 3, the lithotripsy table 113b docked to the urological treatment table 113a and the x-ray unit is illustrated. The two tables 113a and 113b are docked and then latched together for stability providing a platform for a moveable planar surface or a "sled" 107. The docking latch 112 is dropped into place once the tables are docked together. Although the preferred embodiment describes the use of a docking latch 112, any functionally equivalent latching means may be used so long as the latching means provides stability for the tables and allows the use of the sled 107.

To initially locate the kidney stone X, the patient P is placed on the sled 107. The sled 107 is located at position 1, which is at the urological table 113a. During the localization procedure, the patient P must remain essentially immobile. Immobility is achieved by locking the sled 107 into position and by the careful placement of the patient P. The upper portion of the patient's body is positioned against a headrest 201, while the patient's legs are placed over the leg rest 202. This allows the patient's back to rest directly and comfortably on the upper surface of the sled 107. In addition to the relative comfort, the patient is made immobile.

Once the patient P is placed such that the kidney stone X is generally centrally located over the fluoroscope 102, a fluoroscopic exposure is taken of the stone X. The precise position of the stone X is achieved by taking two x-ray views with the tomo head 101 at a +9 degee oblique setting 101a and a −9 degree oblique setting 101b. After the two oblique views are acquired, the processing unit of the x-ray control unit 105, shown in FIG. 1, calculates the coordinates of the stone X within the body.

Initially, the stone X is marked on the dual monitors 106 with a marking symbol, such as a cross-hair marker. The coordinates are then calculated with reference to radiopaque markers embedded in the surface of table 113a. After the coordinates have been calculated, the patient P is moved into position 2, via the sled 107, onto the lithotripter housing 103. The sled 107 is then locked into position. The stone coordinates obtained from the x-ray prelocalization are sent to the lithotripter unit 127 for positioning the stonebreaker focal point.

FIG. 4 illustrates the positioning of the acoustical lens 205 and stone-breaking assembly 301 within the lithotripter control housing 103.

In the preferred embodiment, the housing 103 is provided with wheels 310, thus increasing the mobility of the lithotripter system 100. However, the wheels 310 are not essential to the practice of the present invention.

A portion of the housing 103 is utilized by the several electronic control units. A system controller 307, a pulse modulator 306, a servo amplifier 308 and the servo control unit 309 are located within the housing 103. All of the units are typically constructed from well-known prior art circuitry and sequences.

The servo control unit 309 drives the servo amplifier 308, which in turn controls a positioning system 303. The control unit 309 employs algorithms consisting of prior art sequences typically used to control robotic mechanisms. The positioning system 303 controls the positioning of the stone-breaking assembly 301 in manner similar to the computer control of a robotic arm. The use of robotic algorithms with the positioning system 303 virtually eliminates patient handling, since a 5-axis positioning of the acoustical lens 205 is now available. The ability to rotate or otherwise position the focussed shock wave additionally aids in the minimization of pain and the shortening of treatment duration. Thus, for example, if a kidney stone is found to lie in close proximity to a rib, the positioning system 303 is able to compensate and rotate to an alternative position, thereby avoiding the rib.

Additionally, the housing 103 also functions as a base for the lithotripter table 113b. An area located directly over a flexible water containment enclosure (waterbag) 302 is open, providing for direct patient contact with the water bag 302. The patient's back is positioned over the water bag 302, allowing the weight of the patient to force the bag 302 downward causing the waterbag 302 to conform to the shape of the patient's back. This provides necessary coupling between the water bag 302 and the patient so that the shockwaves propagated through the water bag 302 will travel uninhibited to and through the patient's body, ultimately shattering the kidney stone.

Referring to FIG. 5, the stone breaking apparatus 301 is illustrated. The assembly 301 is comprised of the acoustical lens 205, a piezoelectrical crystal array 405, a coupling means 407, a mechanical standoff 403 and a supporting back plate 404.

The acoustical lens 205 is fabricated in the shape of an ellipsoid. In the preferred embodiment, the lens 205 is shaped from a singular piece of aluminum alloy. However, other materials could be used that have characteristics that allow the propagation and focussing of energy from piezoelectric crystals and still be within the scope and spirit of the present invention.

The shape of the lens 205 is generally ellipsoid, such that the concave inside surface 408 is defined by the following equation:

$$y = 13.525 - (182.931 - 1.060 \, x^2)^{\frac{1}{2}}$$

The lens 205 of the preferred embodiment measures approximately 18.75 inches from flange to flange with a depth of approximately 3.95 inches from top to bottom. A center opening 401, allows for placement of an ultrasonic probe approximately 3.31 inches in diameter. The stone breaking apparatus 301 is provided with an upper flange 402, which allows the lens 205 to be positioned within the apparatus 301 itself. The assembly 301 is held together with a supporting back plate 404.

Referring to FIG. 6, section A—A of FIG. 5 is illustrated. The water bag 302 is illustrated to show its relationship to the acoustical lens 205. The acoustical lens 205 is positioned such that the water bag 302 positioned directly on the concave upper surface 408 of the lens 205. The back support plate 404 holds the stone breaking apparatus 301 together.

In the preferred embodiment, the water bag 302 is comprised of two independent bags. There is an inner bag 1 that is attached by being pinched between the top lens flange 402 and a ring, which is then secured to the lens 205 with screws. The outer bag 2 is secured to the outside diameter of lens 205 with a hose clamp-line strap. This outer bag 2 serves as a back up seal in case the inner bag 1 should rupture.

Positioned on the bottom surface of the acoustic lens 205 are the piezoelectric crystals 405. In the preferred embodiment, the piezoelectric crystals 405 are circularly arranged in an array of approximately 720 square pillars or elements. The preferred embodiment presently uses a C5800 ceramic for the crystals 405. However, any ceramics demonstrating the same or functionally equivalent characteristics may be used and still be within the spirit and scope of the present invention.

After piezoelectric crystals 405 have been bonded to the bottom surface of the lens 205, the crystals 405 are encapsulated. This provides electrical insulation and seals the crystals 405. Typically, a generic material such as an RTV silicon elastomer is used to encapsulate the crystals 405.

An acoustical matching layer 410 may be placed on the concave surface 408 of the lens 205. The matching layer 410 may comprise a generic type of epoxy or plastic used to provide a better acoustic impedance match between the lens material and the water. Of necessity, this material is dependent on the lens material. Although the acoustic matching layer 410 is illustrated in the preferred embodiment of the present invention, is it not essential to the practice of this invention. However, the epoxy or plastic when used, needs to have similar matching characteristics to the material selected for the lens 205. Advantageously, this layer reduces the sharp transition zone at the water/lens interface.

Referring now to FIG. 7, a perspective view of the piezoelectric crystals 405 mounted on the bottom surface of the acoustical lens 205 is described. After the lens 205 has been fashioned, the piezoelectric crystals 405 are positioned. In the preferred embodiment, the crystals 405 are positioned in a circular array similar to a mosaic, of approximately 720 square pillars. Each pillar occupies an area of 0.09 square inches. The volume is approximately 0.045 cubic inches. Alternatively, a single large crystal may be shaped to cover the button surface of the lens 205. As a third alternative, several larger pieces may be utilized. However, the preferred embodiment provides 720 pillars to allow for easier replacement of blocked pillars. The arrangement is preferred since a broken pillar is much easier to replace. The mosaic of crystal pillars decreases the lateral stress and if any one of the pillars should crack, the crack will not propagate through the entire piezoelectric crystal 405 array. In the preferred embodiment, the crystals 405 are bonded to the bottom surface of the lens 405 using an adhesive available under the trade name of Emerson Cummings 1264 Epoxy.

Once the crystals 405 are positioned, all the pillars are wired in parallel providing for parallel exitation from a single power supply. The parallel wiring is accomplished by placing a voltage coupling means on the bottom of the crystals 405. In the preferred embodiment, a copper mesh 409 is bonded to the top of the crystals 405 using a silver epoxy. However, any voltage coupling means accomplishing the same objective may be used and still be within the scope of the present invention.

To produce a shockwave sufficient to shatter a kidney stone, the piezoelectric crystals 405 must be exited. FIGS. 8–10 illustrate the crystal triggering circuit, the resultant wave form and the timing sequence for the triggering pulse.

Referring to FIGS. 8 and 10, a voltage supply 501 is used to excite the piezoelectric crystal 508. The voltage supply 501 of the preferred embodiment is a Phazon model PM3020A. The voltage supply 501 is coupled to a hydrogen spark gap tube 503, the inductor 504 and the piezoelectric crystal 508. The pulse generating circuit for the spark gap tube 503 is described in FIG. 9. Although a Phazon model PM3020A is used in the preferred embodiment, and voltage supply or ramp source having similar characteristics would be acceptable for use with the present invention. The voltage supply 501 provides a constant current source manually adjustable from 1 to approximately 60 milliamps. Furthermore, the voltage supply provides an output voltage range of to 160 VDC in approximately 128 equal steps with a tolerance of a +/−3% of setting. The output current is adjustable within the range of 0–25 milliamps. The current must and is stable within a +/−3% of the set current. Transient response is less than 2 milliseconds. The voltage supply provides for an input line frequency of 47–67 hertz. Furthermore, the supply 501 comprises an under voltage protection.

The initial trigger pulse comes from the controller panel 600 of the lithotripter system 100. The trigger pulse controls the ramp output of the voltage supply 501. When the voltage supply 501 receives the trigger pulse, the voltage supply turns on and ramps up to a predetermined voltage. As the voltage supply ramps, the voltage across the capacitive load, which in this case is the crystal 508, follows a similar ramp profile. Additionally, the spark gap tube 503 encounters a similar ramp voltage. Once the voltage across the spark gap tube 503 has reached its characteristic ionization voltage, the spark gap tube 503 triggers, creating a short circuit between the spark gap tube 503, an inductor 504 and the crystal 508. When the spark gap tube 503 triggers, a delayed reset pulse is sent to terminal 502. This allows the spark gap tube 503 to be reopened following the discharge of the stored current into the crystal 508. This permits a second pulse or any additional pulses with minimal time delay.

FIG. 9 illustrates a timing diagram of the pulse sequences used for triggering the spark gap tube 503 and the piezoelectric crystal 508. Pulse sequence A illustrates the initial triggering pulse from the controller 600. Sequence B illustrates the ramp up of the voltage supply 501. Sequence C illustrates the corresponding ramp up of the spark gap tube 503. Sequence D shows the generation of the time delay initiated by the firing of the spark gap tube 503. Following this time delay, a reset pulse is sent to the spark gap tube 503 via terminal 502.

FIG. 10 illustrates corresponding voltage ramp across the crystal 503 as the voltage supply ramps. A crystal absorbs the voltage, flexing continuously until the spark gap tube 503 triggers. Once the tube 502 is triggered, the output voltage across the capacitive load of the crystal 508 is rapidly discharged through inductor 504. The reduction of the voltage on the crystal 508 from its peak 510 to its relaxed state 511 should be essentially instantaneous.

This is because the crystal 508 will instantaneously return to its normal relaxed state when the voltage is removed from across the crystal 508.

An advantage of the pulsing circuit of FIG. 8 is that due to the relative slow ramp time of the voltage supply and the crystal 508 there is minimal stress applied to the crystal 508 until just prior to triggering.

The slow, continuous ramp provides for a continuous rate of "deformation" of the crystal 508. This is opposed to a rapid deformation of the crystal 508 which could result in premature triggering. Furthermore, when the voltage across the crystal 508 is removed, the theoretical circuitry should affect an instantaneous return to the normal relaxed state of the crystal. To effect a rapid discharge of the crystal voltage, inductor 504 is chosen to produce a critically damp circuit, with the resistance of such a circuit being the intrinsic resistance of the crystal 508. In the preferred embodiment, the inductor 504 is approximately one microhenry. Once the voltage is removed from the crystal 508, this instantaneous return to the normal state produces a disruptive or sonic wave front. This wave front is propogated through the acoustical lens 205 focussing to a narrow focal point coincident with the kidney stone, thus providing the necessary energy to shatter the kidney stone.

Thus what is described is a lithotripsy system having an improved power supply for energizing piezoelectric crystals.

We claim:

1. In a lithotripsy system having a piezoelectric means for generating an energy beam upon expansion and a focussing means for focussing said energy beam on a calculus in a patient, said focussing means attached to said piezoelectric means, the improvement comprising a means for supplying power to said piezoelectric means, said power supply means comprising:

a trigger pulse generating means for generating a trigger pulse;

voltage supply means, coupled to said trigger pulse generating means, for generating a ramped output voltage upon receiving said trigger pulse;

said piezoelectric means coupled in parallel with said voltage supply means and contracting as said ramped output voltage is received; and a spark gap tube means, coupled in parallel with said voltage supply means, for creating a short circuit when said ramped output voltage reaches a predetermined level thereby rapidly decreasing the voltage across said piezoelectric means causing said piezoelectric means to expand thereby generating said energy beam.

* * * * *

UNITED STATES PATENT AND TRADEMARK OFFICE
CERTIFICATE OF CORRECTION

PATENT NO. : 4,945,898
DATED : August 7, 1990
INVENTOR(S) : James W. Pell, et. al.

It is certified that error appears in the above-indentified patent and that said Letters Patent is hereby corrected as shown below:

Title page, item [57], col. 2,

[57] In the Abstract:, line 5: Delete "form" Insert in place thereof --from--

Signed and Sealed this

Twelfth Day of September, 1995

Attest:

BRUCE LEHMAN

*Attesting Officer*      *Commissioner of Patents and Trademarks*